United States Patent [19]

Ramsden

[11] Patent Number: 4,713,345

[45] Date of Patent: Dec. 15, 1987

[54] FERMENTATION METHODS AND APPARATUS

[75] Inventor: Steven L. Ramsden, Muscatine, Iowa

[73] Assignee: Grain Processing Corporation, Muscatine, Iowa

[21] Appl. No.: 760,288

[22] Filed: Jul. 29, 1985

[51] Int. Cl.$^4$ ............................................. C12M 1/02
[52] U.S. Cl. ..................................... 435/305; 435/316
[58] Field of Search .............. 435/316, 257, 302, 305, 435/306, 307; 426/11, 12, 13, 14, 15, 16; 422/225, 226

[56] References Cited

U.S. PATENT DOCUMENTS

| | | | |
|---|---|---|---|
| 2,155,134 | 4/1939 | Karsch | 435/316 X |
| 3,219,319 | 11/1965 | Ash | 435/316 X |
| 4,151,084 | 4/1979 | Probstein | 210/97 |

OTHER PUBLICATIONS

*Biotechnology and Bioengineering*; vol. XXVI, pp. 640–641, Bungay and Millspaugh; 1984.
*Biotechnology and Bioengineering*; vol. XXI, pp. 1081–1084, 1979.
Biotechnology Letters; vol. 6, No. 6, pp. 389–394, Diaz, et al. 1984.
Ind. Eng. Chem. Process Des. Dev., pp. 58–67 1983.

*Primary Examiner*—Alan Cohan
*Attorney, Agent, or Firm*—Neuman, Williams, Anderson & Olson

[57] ABSTRACT

Fermentation reactions are conducted by introducing into a fermentation vessel a flocculating microorganism and a fermentable medium and continually withdrawing fermented broth from the vessel through a conduit which is disposed at an angle of at least 60° but less than 90° from the horizontal.

7 Claims, 6 Drawing Figures

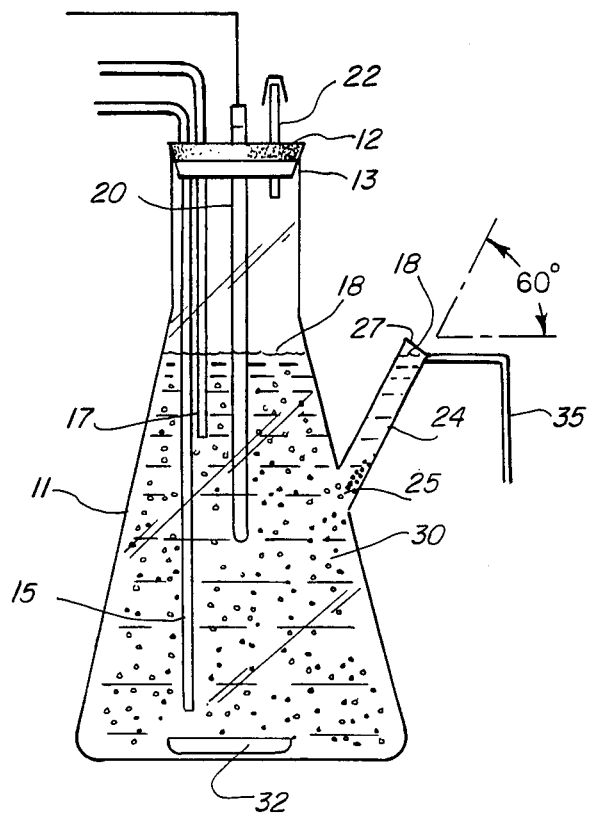
FIG. 1
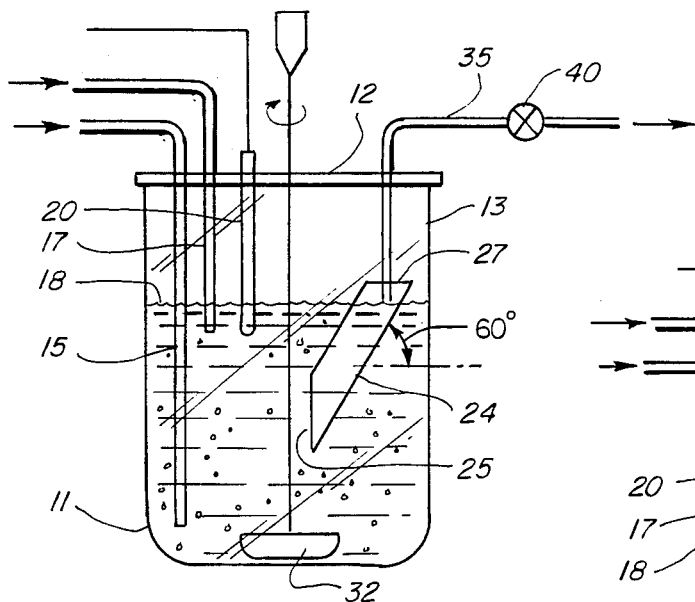
FIG. 2
FIG. 3

| BOTTOM OPENING GREATER THAN 90° FROM HORIZONTAL | BOTTOM OPENING AT 90° FROM HORIZONTAL (OR LESS) | ANGLED CONDUIT WITH GAS ESCAPE HOLE(S) |
|---|---|---|
| 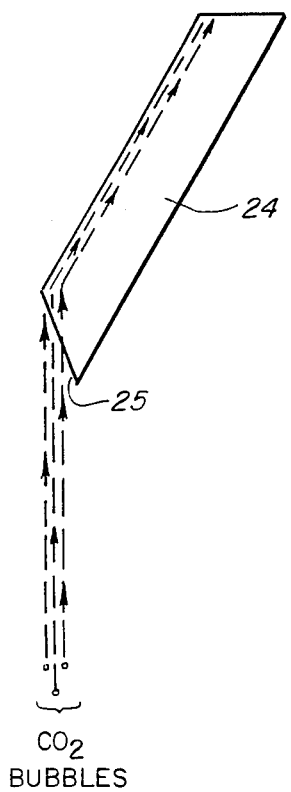 | 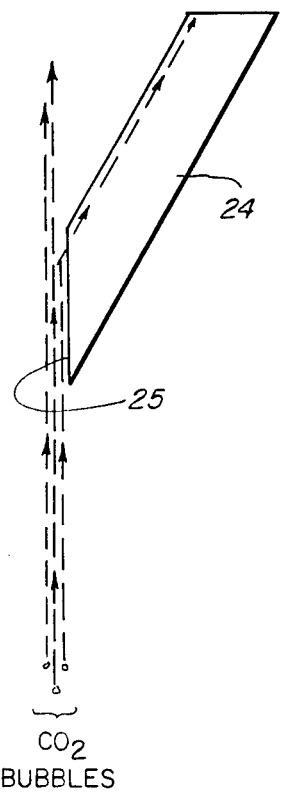 | 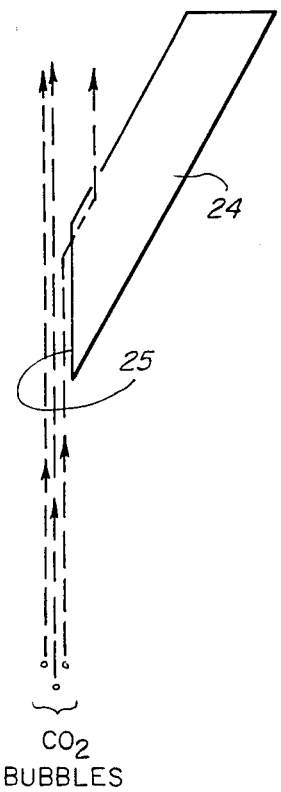 |
| FIG. 4 | FIG. 5 | FIG. 6 |

FERMENTATION METHODS AND APPARATUS

This invention relates to methods and apparatus for conducting fermentations.

Fermentation procedures are known wherein a fermentation medium is fermented with microbes to produce various products. For example, ethanol is produced from corn by fermentation procedures. Continuous stirred tank reactors (CSTR) have been found particularly useful for conducting fermentations. In a typical continuous stirred tank reactor, an active culture of a microorganism is maintained and a substrate feed containing appropriate fermentable carbohydrates and nutrients is continually metered into the reactor. A very homogeneous mixture of the microorganism and fermentation broth is achieved within the reactor by means of suitable agitation means which can involve mechanical agitation as provided by impellers and the like. The feed rate of the fermentation medium is regulated depending on the size of the reactor and the required residence time for accomplishing the fermentation reaction.

A major problem with a continuous stirred tank reactor employing cell recycle is to attain and efficiently maintain a high concentration of cell mass in the reactor. In some systems a separate chamber is employed wherein the fermented broth is separated from the active fermentation microorganisms which are then recycled to the bioreactor. Separation of the fermented broth and fermentation microorganisms has also been accomplished by the use of centrifuges and diffusion membrane techniques. Separation techniques such as these usually require the use of recirculating pumps, which not only add to the cost but are often a source of contamination. Pumps have always been notorious sources of contamination.

The use of a separate separation tank or chamber increases the cost of the operation and involves maintenance. The centrifuge and separating membrane techniques do not differentiate between desirable and undesirable microorganisms and often single cell contaminants are not separated by these techniques.

Another drawback to such separation techniques is the environmental changes inflicted on the fermentation microorganisms. Thus, with the separate separating chamber, the organisms are transferred from active state to a dormant state for a lengthy period of time. During such lengthy periods development and propagation of contamination in the fermentation system can occur. With the centrifuge or membrane separating procedures, the microorganisms are subjected to shearing forces and/or changes in pressure. These environmental changes may contribute to reduced cell productivity or even death.

It is a major object of this invention to provide novel methods and apparatus for conducting fermentations.

It is another object of the invention to provide continuous fermentation methods and apparatus which afford attainment and efficient maintenance of a high concentration of cell mass in a convenient manner and which does not involve high capital investment costs or high maintenance costs.

A still further object of the invention is to provide continuous fermentation methods and apparatus which afford high productivity.

It is still another object of this invention to provide novel methods and apparatus for conducting continuous fermentations with cell recycle.

Another object of the invention is to provide fermentation methods and apparatus wherein recycle of fermentation microorganisms is accomplished without requiring the use of recirculating pumps.

Yet another object of the invention is to provide fermentation methods and apparatus wherein the fermentation microorganisms are recycled without being subjected to dramatic or prolonged environmental changes.

Another object of the invention is to provide fermentation methods and apparatus wherein recycle cell contaminant microorganisms are readily separated from the desired fermentation microorganisms.

Thus, the invention in its preferred embodiment provides a method for conducting fermentation reactions which comprises conducting a continuous fermentation reaction in a vessel and continuously withdrawing fermented broth from the vessel through a relatively small effluent discharge conduit which is disposed at a defined angle. The fermentation vessel or fermentor is provided with means for introducing a fermentation medium and with means for agitating the contents thereof. An effluent discharge conduit communicating with the interior of the vessel is provided for conducting fermented broth from the fermentor with minimal loss of the micorbial culture. The discharge conduit is disposed at an inclined angle of at least 60° but less than 90° from the horizontal whereby the flocculating microorganism cells which collect in the discharge conduit are returned to the fermentation reaction.

Fermentation reactions are conducted in accordance with the invention by introducing into a continuous fermentation vessel a flocculating microorganism and continuously metering in a fermentable medium, agitating the contents within the fermentation vessel, and continuously withdrawing fermented broth from the vessel through a discharge conduit which is disposed at an angle of at least 60° but less than 90° from the horizontal.

Preferred embodiments of the fermentation apparatus of this invention are illustrated in the drawings wherein:

FIG. 1 is a diagrammatic side view of an illustrative type of fermentation apparatus for use in accordance with the invention.

FIG. 2 is a diagrammatic side view of another illustrative type of fermentation apparatus in accordance with the invention.

FIG. 3 is a diagrammatic side view of another illustrative type of fermentation apparatus in accordance with the invention.

FIGS. 4, 5 and 6 are schematic illustrations showing gas flow with respect to the inlet opening of the inclined effluent discharge conduit.

As shown in FIG. 1, the fermentation reaction vessel 11 has a tapered frustro-conical shape but it can be of other shapes such as cylindrical. The fermentor 11 can be formed of glass, stainless steel and other suitable materials. The size of the fermentor 11 will, of course, depend upon the scale of the fermentation being conducted therein. Closure element 12 seals the top opening 13 of the fermentor. Substrate introduction line 15 extends through closure 12 and into the fermentor to a point near the bottom. A fermentation medium together with suitable fermentation organisms is introduced through line 15. A second line 17 also extends through closure 12 and into the fermentor a sufficient distance so that it terminates a short distance below the normal liquid level 18 maintained in the fermentor. Acids or bases can be introduced through line 17 so as to maintain a desired pH condition in the reaction mass, and a pH probe 20 can be inserted through closure 12 to monitor the pH. Vent 22 projects through the vessel closure 12 whereby gas produced in the fermentation can escape.

Projecting angularly outward from the fermentor 11 and communicating with the interior thereof is a discharge conduit 24 which has a lower or inlet opening 25 and a top discharge opening 27. This discharge conduit 24 serves as a microorganism retention device and for effluent discharge. The effluent discharge conduit 24 is disposed at an angle of at least 60° but less than 90° from the horizontal. The inlet opening 25 of the angled conduit is preferably disposed at a 90° angle or less from the horizontal to minimize turbulence within the conduit. The greater the flow turbulence within the angled discharge conduit the less settling and retention of the flocculated microorganism.

The lower end of the discharge conduit extends below the surface of the liquid within the fermentor while the top opening 27 of discharge conduit 24 is disposed at the same elevation as the normal operating liquid level 18 within the fermentor. The fermented broth effluent is discharged from the top discharge opening 27 of the conduit by gravity flow as the volume of liquid in the fermentor increases. Thus, the rate of discharge depends on and is substantially the same as the rate at which the fermentable substrate is introduced into the fermentor. The dimensions of the effluent discharge conduit 24 are not particularly critical and the ratio of length to diameter can range from about 3 to 10:1 or more. However, the discharge conduit is much smaller in size than the size of the fermentation vessel. Preferably, the volume of the effluent discharge conduit is on the order of not more than 5–8% of total working volume of the fermentation vessels. An important advantage of a relatively small effluent discharge conduit is that a differentiation is inherently effected between single cell contaminating microorganisms and the desired flocculating microorganisms employed for the fermentation. With the short residence time of the conduit (the flow time from the entrance of the conduit to the exit) due to the conduit's small size the single cell contaminants do not have the time to settle out from the fermented broth. Thus, the conduit allows for the single cell organism to be flushed out of the fermentation system in the effluent overflow while the desirable flocculating organim is retained.

In conducting a fermentation reaction in accordance with this invention, a flocculating fermentation organism 30 is placed into the fermentor and a substrate feed or fermentation medium introduced at a controlled rate through feed line 15. The fermentation medium containing appropriate fermentable carbohydrate(s) and nutrients can be continuously metered into the fermentor.

The microorganisms which are employed can be any of the known flocculating microorganisms which, as is known, means microorganisms which have the ability to adhere together and form macroscopic particles. The particular microorganisms to employ will, of course, depend on the fermentation product desired and likewise the fermentation medium will be one which contains carbohydrates which are susceptible to undergoing fermentation by the particular organism or organisms. Thus, for example, in conducting a fermentation to produce ethanol, flocculating microorganisms such as Saccharomyces, Zymomonas, Kluyveromyces and Pachysolen can be advantageously used. Likewise, the fermentation medium can comprise carbohydrate sources such as dextrose, maltose, sucrose, fructose, lactose, xylose, soluble starch and the like together with various nutrients.

The present invention has wide applicability for numerous known fermentations including, for example, amino acids, enzymes, organic acids, various solvents, etc.

During the fermentation reaction, agitation is preferably provided within the reactor such as by impeller 32. The agitation should be sufficient to provide a homogeneous mixture of the fermentation broth and the flocculent fermentation organisms. A portion of this mixture is continually entering the opening 25 of the effluent discharge conduit 24. When the mixture enters this non-agitated, quiescent atmosphere of the effluent conduit, the flocculent organisms rapidly settle to the lower end of the conduit and because of the angle of disposition thereof, the settled mass slides down the conduit and re-enters the fermentation reactor, thus being retained within the system. By retaining the flocculent microorganism the active fermenting cell mass builds up in the fermentor resulting in an extremely rapid fermentation time. Fermented broth (effluent) exits the top of the conduit 24 through opening 27 and is removed from the system via line 35 at the same rate as fresh substrate is being pumped into the fermentor.

FIG. 2 of the drawing shows another illustrative type of apparatus for conducting fermentations in accordance with this invention. In the apparatus of FIG. 2 the inclined effluent discharge conduit 24 is disposed within the fermentor and the fermented broth is pumped at a controlled rate through discharge line 35 by means of pump 40.

FIG. 3 of the drawing shows apparatus similar to that of FIG. 2 with the inclined effluent discharge being positioned within the interior of the fermentor in such position that the fermented broth discharges through discharge line 35 by gravity flow.

The following examples further illustrate the invention and the advantages thereof.

EXAMPLE 1

The fermentation vessel consisted of a 1.0 liter flask (Kimax No. 26650) substantially as shown in FIG. 1 of the drawing with continual agitation (magnetic drive) and pH control. Protruding out from the side of this flask at an angle of approximately 60° from the horizontal was an effluent discharge conduit. This discharge conduit had an inside diameter of 0.8 centimeter and an average length of 8.0 centimeters. Thus, the total volume of the discharge conduit was slightly over 4.0 cubic centimeters which is less than 0.5% of the total volume of the fermentation vessel.

An active culture of an ethanol-producing, flocculent yeast, *Saccharomyces uvarum* (GPC 86), was placed in the fermentor. A fermentation substrate was then continually pumped into the vessel at a flow which was based upon the dilution rate to be examined. This particular substrate consisted of 16% dextrose (dry solids) weight/volume, as the fermentable carbohydrate and 0.5% yeast extract (dry solids) weight/volume, plus appropriate inorganic salts.

At the upper end of the effluent discharge conduit, fermentation effluent was continually removed at a rate equal to the rate of substrate feed. The following table gives the fermentation parameters and results.

TABLE 1

Flocculent Yeast

| Hours of Continual Substrate Feed | Dilution Rate ($h^{-1}$) | Dextrose Feed, g/l | Temperature °C. | Cell Mass, g/l Fermentor | Cell Mass, g/l Effluent | Floc Retention Efficiency, % | Effluent % Alcohol v/v |
|---|---|---|---|---|---|---|---|
| 26 | 0.18 | 160 | 28 | 7.68 | 0.74 | 91.2 | 6.41 |
| 44 | 0.18 | 160 | 28 | 23.28 | 0.75 | 96.9 | 8.05 |
| 52 | 0.18 | 160 | 28 | 27.64 | 0.60 | 97.9 | 8.52 |
| 68 | 0.18 | 160 | 28 | 32.35 | 0.67 | 98.0 | 8.86 |
| 73 | 0.18 | 160 | 28 | 32.73 | 0.82 | 97.6 | 8.95 |
| 77 | 0.18 | 160 | 28 | 35.94 | 0.63 | 98.3 | 8.81 |

The % Floc Retention Efficiency data in Table 1 is an expression from the following calculation:

$$\frac{\text{Cell Mass in Fermentor}}{\text{Cell Mass in Fermentor + Cell Mass in Effluent}} \times 100$$

It is evident by the cell mass data presented in Table 1 that the fermentor provided with the angled effluent overflow tube efficiently retained flocculent yeast within the fermentor. After the period of rapid growth (beyond 26 hours), this system consistently exhibited a floc retention efficiency of over 96%. These data also demonstrate that floc retention is efficient even at high concentrations of cell mass (greater than 30 grams (dry solids) yeast/liter).

By allowing the flocculent yeast mass to accumulate in the reactor a rapid fermentation was achieved, producing over 8.5% ethanol volume/volume with only a 5.5 hour fermentor residence time.

EXAMPLE 2

The procedure and apparatus of Example 1 was followed using an ethanol-producing, flocculent bacterium, *Zymomonas mobilis* (GPC 495). Various dilution rates were used while employing 13.5 to 14% weight/volume fermentable carbohydrate substrate feed. Table 2 summarizes the results:

ent discharge conduit volume being approximately 4.0 cubic centimeters, the dilution rates employed corresponded to effluent flow residence times through the conduit of 0.96 minute down to 0.67 minute. This fermentation was conducted for 96 hours and at the end of this period it appeared that this system would have continued to provide a floc retention efficiency of over 90%.

EXAMPLE 3

This continuous fermentation employed a 1.5 liter, straight-walled fermentation vessel similar to that illustrated in FIG. 2 of the drawing with a shaft-driven impellor as the means of agitation. The vessel was provided with an outwardly and upwardly projecting effluent discharge conduit having a diameter of 1.7 cubic centimeters and an average length of 9.5 centimeters. This effluent discharge conduit was positioned at a 65° angle from horizontal and in a direction such that the lower opening of the conduit faced away from the direction of the reactor vortex and the opening was vertical, thus reducing the amount of fermentation carbon dioxide that could enter the conduit. The top opening of the angled effluent discharge conduit was placed above the volume line of the reactor so that fermented broth flowed from the discharge conduit at the same rate as substrate flowed into the reactor. The actual working length of this angled conduit was 6.6 cubic centimeters for an actual conduit volume of 15 cubic centimeters.

An active culture of the ethanol-producing, flocculent yeast (GPC 86) was placed into the reactor. Substrate feed-in was started at 4.0 milliliters per minute for a fermentor dilution rate of 0.2 $h^{-1}$. This residence time of 5.0 hours was maintained throughout this fermentation while fermentable carbohydrate concentrations of 140 grams per liter and 160 grams per liter were employed.

Table 3 summarizes the results of this fermentation.

TABLE 2

Flocculent Zymomonas

| Hours of Continual Substrate Feed | Dilution Rate ($h^{-1}$) | Dextrose Feed, g/l | Temperature °C. | Cell Mass, g/l Fermentor | Cell Mass, g/l Effluent | Floc Retention Efficiency, % | Effluent % Alcohol v/v |
|---|---|---|---|---|---|---|---|
| 17 | 0.25 | 140 | 31.5 | 6.59 | 0.72 | 90.2 | 7.06 |
| 24 | 0.25 | 140 | 31.0 | 9.52 | 0.48 | 95.2 | 8.21 |
| 42 | 0.33 | 140 | 31.0 | 12.85 | 0.34 | 97.4 | 7.89 |
| 48 | 0.33 | 140 | 31.0 | 14.89 | 0.38 | 97.5 | 8.03 |
| 68 | 0.36 | 140 | 32.0 | 19.29 | 0.90 | 95.5 | 8.23 |
| 89 | 0.25 | 135 | 27.5 | 13.42 | 1.05 | 92.7 | 8.34 |
| 96 | 0.33 | 135 | 27.5 | 15.43 | 1.13 | 93.2 | 8.21 |

During the early stages of continual fermentation when cell growth was rapid, a retention efficiency of 90% (see Table 2, 17 hours) of the microorganism cells was achieved. During the remaining 72 hours of the fermentation, retention efficiencies ranging from 92.7% to 97.5% with dilution rates as rapid as D=0.36$h^{-1}$ (fermentor residence time of 2.8 hours) were achieved. With the fermentor volume being 1.0 liter and the efflu-

TABLE 3

| | | | | Flucculent Yeast | | | Effluent |
| Hours of Continual Substrate Feed | Dilution Rate (h$^{-1}$) | Dextrose Feed, g/l | Temperature °C. | Cell Mass, g/l | | Floc Retention Efficiency, % | % Alcohol v/v |
| --- | --- | --- | --- | --- | --- | --- | --- |
| | | | | Fermentor | Effluent | | |
| 21 | 0.2 | 140 | 30 | 17.61 | 0.67 | 96.3 | 5.57 |
| 29 | 0.2 | 140 | 30 | 26.80 | 0.42 | 98.5 | 6.71 |
| 45 | 0.2 | 140 | 30 | 30.10 | 0.71 | 97.7 | 7.84 |
| 53 | 0.2 | 140 | 30 | 37.41 | 0.57 | 98.5 | 7.67 |
| 69 | 0.2 | 140 | 30 | 33.32 | 0.91 | 97.4 | 8.18 |
| 77 | 0.2 | 140 | 30 | 33.60 | 0.91 | 97.4 | 8.00 |

The above data demonstrates that the angled effluent discharge conduit does not have to protrude from the side of the fermentor as in Examples 1 and 2, but can be placed therewithin and still provide floc retention efficiencies consistently above 96%. These efficiencies were maintained with a conduit volume that was only 1.0% of the total reactor volume.

As in Example 1, floc retention efficiencies remained above 97% even at cell mass concentrations above 30 grams (dry solids) yeast/liter.

As indicated, the lower opening 25 of the angled effluent discharge conduit is preferably disposed at an angle not exceeding 90° from the horizontal. The angle at which the lower or bottom opening of the effluent discharge conduit is important with respect to turbulence inside the discharge conduit. The more turbulence, in this conduit the less settling of the flocculated microorganisms occurs and with less settling there is a greater loss of the flocculated microorganisms from the conduit.

For example, in an ethanol fermentation, carbon dioxide bubbles are continually being formed and rise to the surface of the fermentor. When these gas bubbles form below the bottom or lower opening (25) of a discharge conduit that is greater than 90° from horizontal, these gas bubbles enter the conduit and travel up the conduit. This is illustrated in FIG. 4. These bubbles create turbulence in the effluent discharge conduit 24 and cause the flocculating microorganisms to rise to the top of the conduit and be lost from the reactor, which is undesirable.

When the bottom opening (25) of the conduit is at an angle of 90° or less from the horizontal, the carbon dioxide bubbles that are formed below this opening have less tendency or opportunity to enter this opening. This is illustrated in FIG. 5. Accordingly, the environment within the discharge conduit is more quiescent. With a less turbulent environment in the discharge conduit the settling and return of the flocculated microorganism to the fermentor is enhanced.

However, even when the bottom opening (25) of the angled discharge conduit is at 90° from the horizontal. some carbon dioxide bubbles can enter the discharge conduit, due primarily to the agitation in the fermentor. To reduce the amount of carbon dioxide that traverses the entire angled discharge conduit, a hole or series of holes can be provided along the top surface of the angled conduit for release of the gas. This is illustrated in FIG. 6. The provision of such gas escape means further reduces the turbulence in the angled discharge conduit and therefore increases the sedimentation and return of the flocculate microorganism to the fermentor.

Those modifications and equivalents which fall within the spirit of the invention are considered to be a part thereof.

What is claimed is:

1. A method of conducting a continuous fermentation reaction which comprises introducing into a fermentation vessel a flocculating microorganism and a fermentable medium, permitting fermentation to occur, and continually withdrawing fermented broth from the vessel through an effluent discharge conduit communicating with the interior of said vessel whereby flocculated microorganism cells separate by sedimentation from the fermentation broth and are retained in the fermentation vessel, said conduit having a volume substantially less than the total working volume of said vessel and being disposed at an angle of at least 60° but less than 90° from the horizontal, and having the inlet opening thereof disposed at an angle not exceeding 90° from the horizontal.

2. A method in accordance with claim 1 wherein the volume of said effluent discharge conduit is not more than about 8% of the total working volume of said vessel.

3. A method according to claim 1 wherein the fermented broth comprises ethanol.

4. A method according to claim 1 wherein the fermented broth is withdrawn through an effluent discharge conduit provided with gas escape means.

5. Apparatus for conducting fermentation which comprises a fermentation vessel provided with means for introducing a fermentable medium into said vessel and with means for agitating the contents thereof, and an effluent discharge conduit communicating with the interior of said vessel, said conduit having a volume substantially less than the total working volume of said vessel and being disposed at an angle of at least 60° but less than 90° from the horizontal, and having the inlet opening thereof disposed at an angle not exceeding 90° from the horizontal.

6. Apparatus according to claim 5 wherein said effluent discharge conduit is provided with gas escape means.

7. Apparatus according to claim 5 wherein the volume of said effluent discharge conduit is not more than about 8% of the total working volume of said vessel.

* * * * *